United States Patent
Coles et al.

[11] Patent Number: 6,103,952
[45] Date of Patent: Aug. 15, 2000

[54] ABSORBENT ARTICLE

[75] Inventors: Peter Coles, Kelkheim-Fischbach; Christopher Bewick-Sonntag, Kelkheim/Ts; Michael Divo, Friedrichsdorf; Helene Karin Costea, Worms; Rainer Walter Max Schone, Koenigstein/Ts, all of Germany

[73] Assignee: The Procter & Gamble Company, Cincinnati, Ohio

[21] Appl. No.: 08/776,100

[22] PCT Filed: Jun. 30, 1995

[86] PCT No.: PCT/US95/08339

§ 371 Date: Jan. 10, 1997

§ 102(e) Date: Jan. 10, 1997

[87] PCT Pub. No.: WO96/02485

PCT Pub. Date: Feb. 1, 1996

[30] Foreign Application Priority Data

Jul. 12, 1994 [EP] European Pat. Off. .............. 94110798

[51] Int. Cl.[7] ........................................... A61F 13/15

[52] U.S. Cl. .................. 604/358; 604/385.1; 604/367
[58] Field of Search .................................. 604/358, 367, 604/378, 385.1

[56] References Cited

U.S. PATENT DOCUMENTS 5,762,641 6/1998 Bewick-Sonntag et al. ........... 604/378

Primary Examiner—John G. Weiss
Assistant Examiner—Dennis Ruhl
Attorney, Agent, or Firm—David M. Weirich; Steven W. Miller; Jacobus C. Rasser

[57] ABSTRACT

An absorbent article especially adapted for users ranging from walking infants to adults in a predominantly laying-down position includes a layer of absorbent material, wherein the average basis capacity of absorbent material located in a back half section of the layer is higher than the average basis capacity of absorbent material located in the front half section of the layer. A liquid barrier means is located between a transverse centerline of the layer and the waist edge of a back sheet to prevent liquids from leaking to the back waist edge.

21 Claims, 10 Drawing Sheets

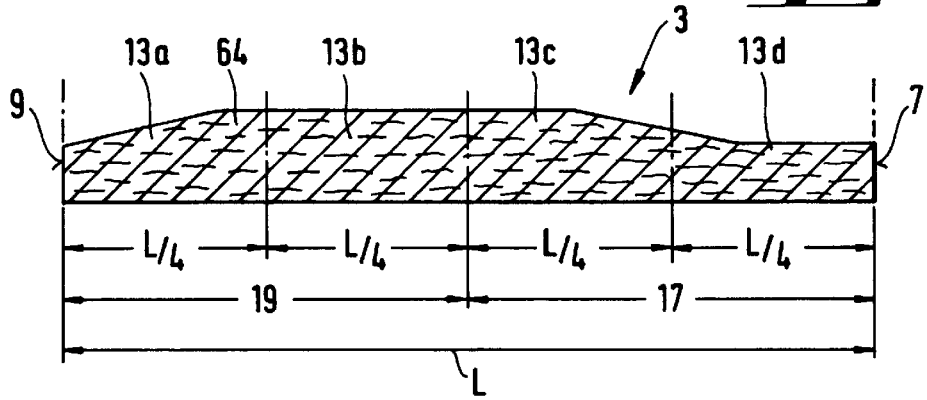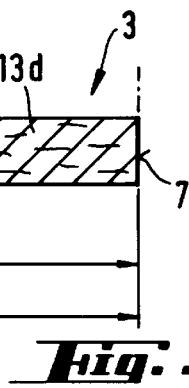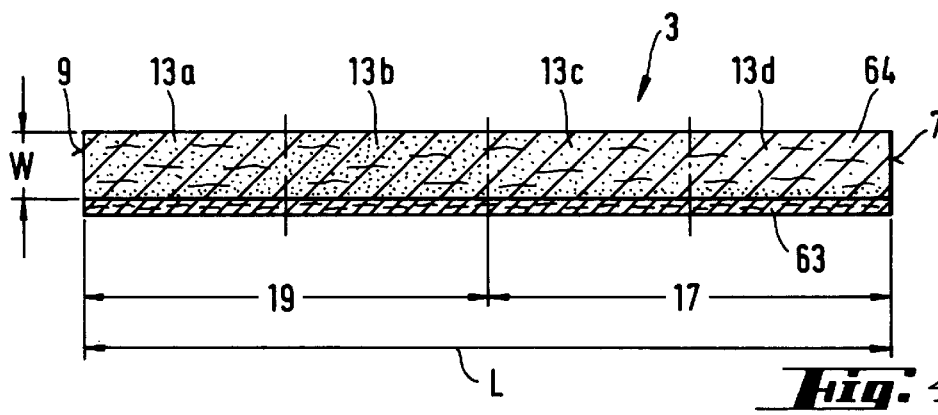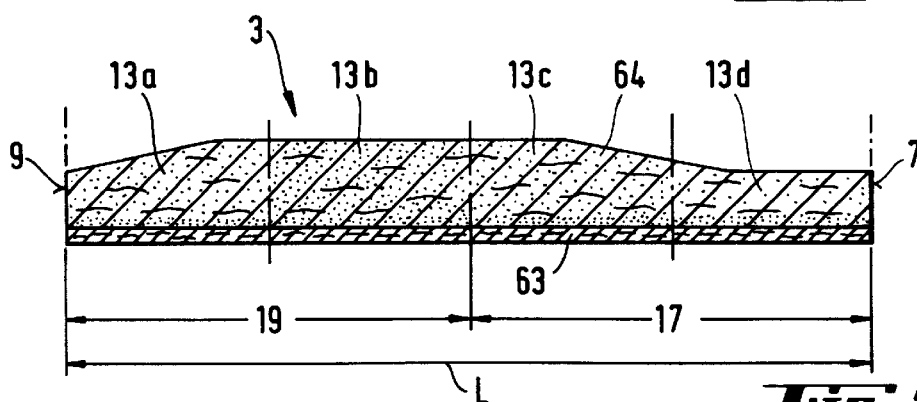

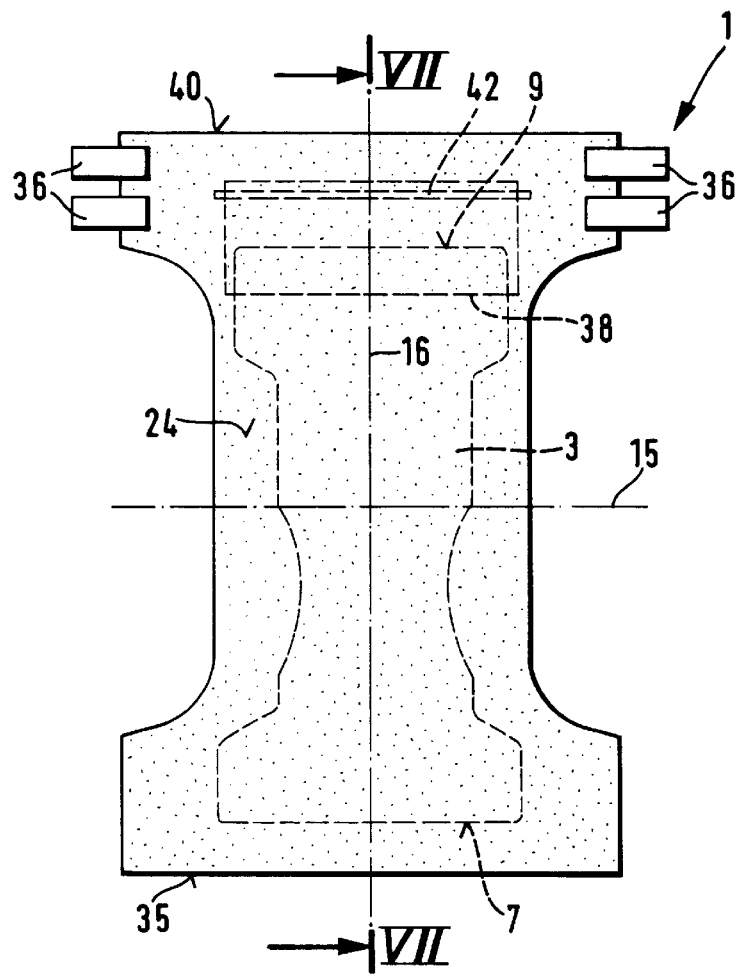
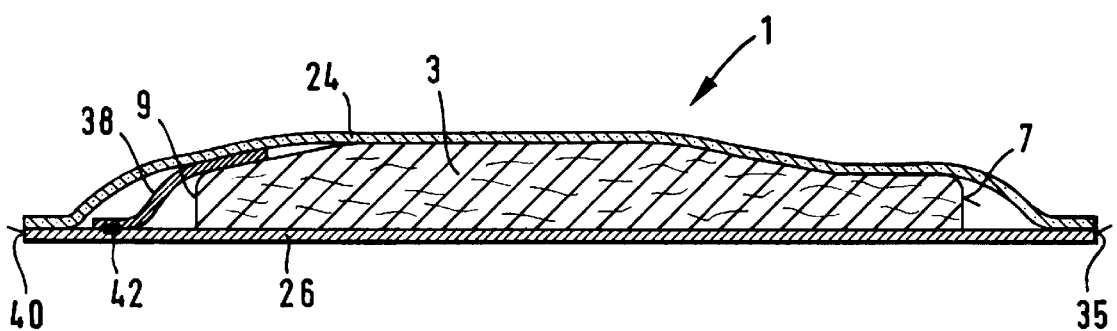

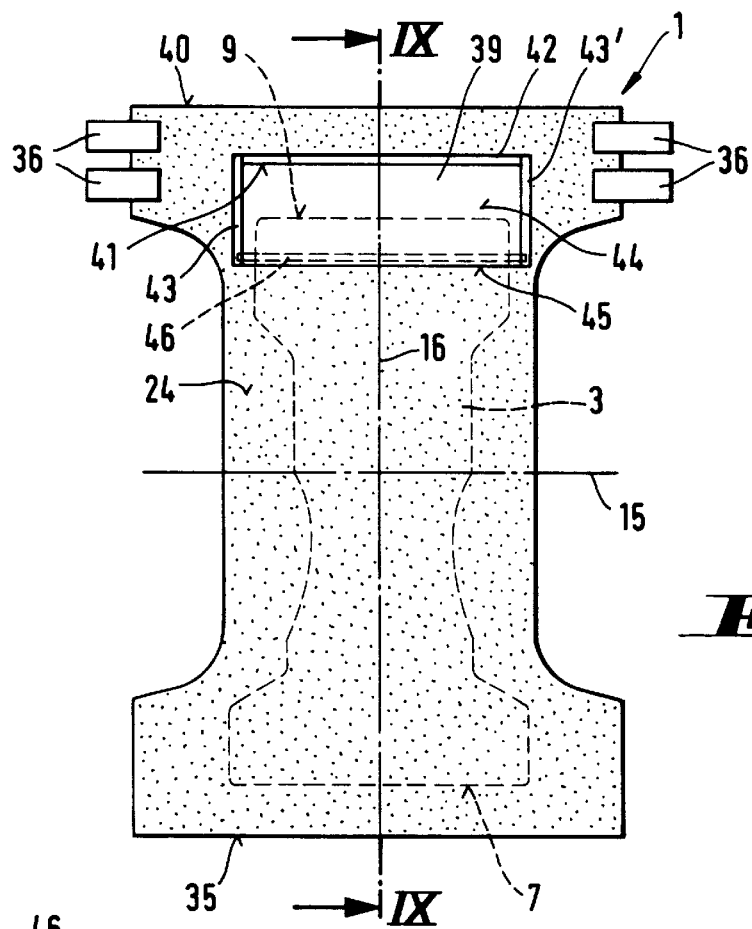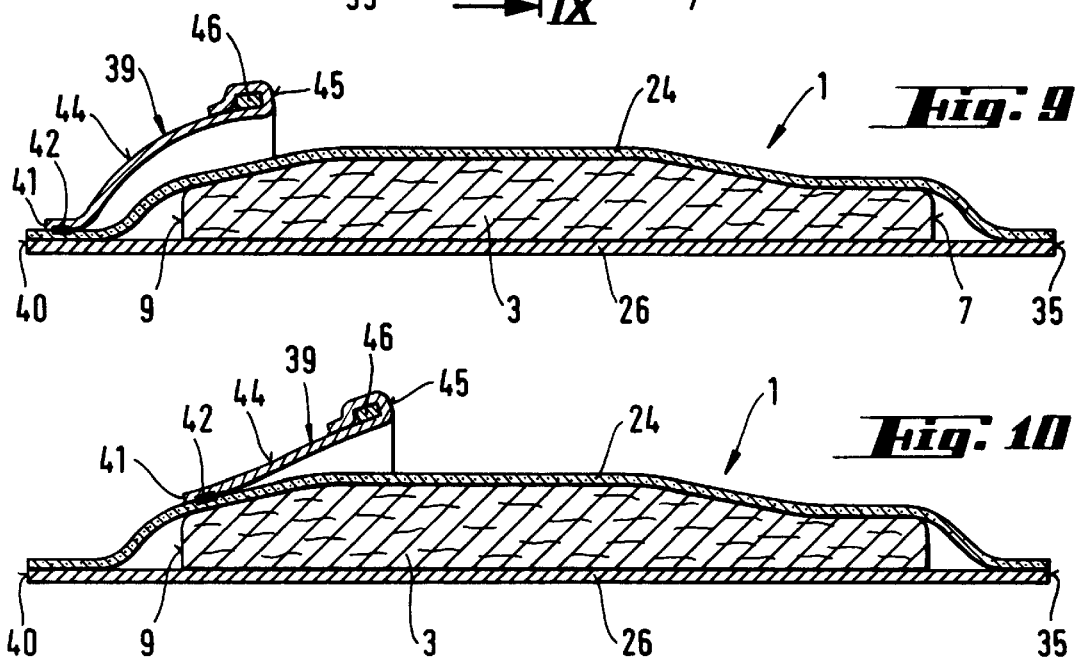

ABSORBENT ARTICLE

FIELD OF THE INVENTION

The invention relates to an absorbent article comprising a liquid permeable topsheet, a liquid impermeable backsheet and an absorbent core comprising a layer of absorbent material, interposed between the topsheet and the backsheet, the backsheet comprising a perimeter having a front waist edge and a back waist edge, the layer of absorbent material comprising:

- a perimeter having two longitudinal edges, a front transverse edge and a back transverse edge,
- a transverse center line located midway between the front transverse edge and the back transverse edge,
- a front half section located between the transverse centerline and the front transverse edge and
- a back half section located between the transverse centerline and the back transverse edge.

BACKGROUND OF THE INVENTION

In the absorbent product technology, many attempts have been made to optimise the absorbent capacity and efficiency of absorbent cores by providing regions of increased or diminished basis weight and density in such cores. Also, it has been attempted to reduce leakage by providing barrier structures to the absorbent products to reduce liquid migration towards and beyond the periphery of the absorbent product.

From EP-A-052 413 it is known that for absorbent products, leakage of liquids along the waist edge can be prevented by providing a barrier sheet located between the topsheet and the backsheet and the waist ends of an absorbent article. The barrier sheet overlies the core at a waist end and prevent liquids from being squeezed out of the transverse edges of the core.

From EP-A-376 022 (Robertson) a unitary waistcap or waistband is known, wherein a unitary piece of elastomeric material extends from the perimeter of the absorbent product towards the core. The single piece of elastomeric material provides a waist elastic as well as a stand-up barrier overlying the topsheet at the waist end of the core.

From U.S. Pat. No. 4,695,278 (Lawson) an absorbent article is known comprising an elasticated stand-up barrier cuff in the leg areas.

From U.S. Pat. No. 4,795,454 (Dragoo) an absorbent article is known comprising an elasticated stand-up barrier cuff that is connected with a proximal edge to the absorbent article, and is located adjacent a gasketing cuff. A liquid-pervious topsheet terminates inboard of the proximal edge of the barrier cuff. Seal means are located along the proximal edge to prevent wicking of liquids underneath the barrier cuff.

From EP-B-0 304 631 it is known to coat and seal lateral portions of a liquid-permeable topsheet with a hot-melt adhesive to prevent lateral leakage of liquids.

In U.S. Pat. No. 4,935,022 (Lash) an absorbent structure is disclosed which has a lower storage layer and an upper acquisition/distribution layer comprising chemically stiffened cellulose fibers and absorbent gelling material. The upper acquisition/distribution layer is of larger surface area than the underlying storage layer. The lower storage layer is formed of an insert, which is placed relative to the upper acquisition/distribution layer such that about 75% of the absorbent gelling material in the lower layer is found in the front two-thirds section of the absorbent structure, and at least 55% of the total amount of absorbent gelling material is found in the front half section.

In U.S. Pat. No. 4,685,915 (Hasse) an absorbent product is disclosed having a core comprising hydrophilic fibers and absorbent gelling material, the core having an area of higher average density and basis weight than the end portions of the core. The area of higher average density and basis weight is located near the center or the front of the absorbent product.

In U.S. Pat. No. 4,834,735 (Alemany) an absorbent core is disclosed having a storage zone and an acquisition region of lower average density and basis weight than the storage zone. The core comprises a mixture of hydrophilic fibers and absorbent gelling particles. The acquisition region is located towards the front of the absorbent core.

In European Patent No EP-B-0 330 675, it is disclosed to introduce absorbent gelling material into specific locations of a horizontal, or x-y plane of an absorbent core using pulsed powder spray guns.

In International patent applications no's WO 91/11163 and WO 91/11165, a dual layer core is disclosed comprising a lower storage layer and an upper fluid acquisition/distribution layer comprising chemically stiffened cellulose fibers, the upper layer being substantially free of absorbent gelling material. The area of the acquisition/distribution layer is between 25% and 100% of the area of the lower storage layer, and is preferably of elongated shape. For adult incontinence products, the acquisition/distribution layer is generally located in the front two thirds of the absorbent article, relative to the backsheet.

In U.S. Pat. No. 4,411,660 (Dawn), an absorbent article is disclosed in which a layer consisting of absorbent gelling material underlies a fibrous layer. The layer of absorbent gelling material can be in the form of particles, fibers or a film.

In International patent application WO 91/04724, a diaper core is disclosed which linearly tapers from a relatively narrow crotch section to a relatively wide back section.

It has been observed by the applicant that especially in the category of adults suffering from incontinence, there is an increased tendency for leakage of the absorbent products when used in lying-down positions of the user. The majority of adults suffering from a severe incontinence are elderly women, for which leakage in these positions is relatively frequent compared to other users.

It is an object of the present invention to provide an absorbent product which provides reduced leakage when used in a lying down position.

It is another object of the invention to provide an absorbent article that is especially adapted for users ranging from walking infants to adults, especially women users, when confined to a predominantly lying down position.

An absorbent article according to the invention is characterised in that the average basis capacity of the absorbent material located in the back half section of the layer of absorbent material is higher than the average basis capacity of the absorbent material located in the front half section of the layer. A liquid barrier means is located between the transverse centerline of the layer and the back waist edge of the backsheet to prevent liquids from leaking to the back waist edge of the backsheet.

The average basis capacity of the absorbent core depends on the amount and on the type of absorbent material that is used in the core and is a measure for the amount of liquid that can be retained per gram of absorbent material. The average basis capacity is measured according to a test method which is based on the official method established by the German "Medizinischer Dienst der Spitzenverbände der Krankenkassen e.V." for reimbursement of incontinence absorbent products. The test method "Prüfmethode Nr. 1/93 MDS-HI Teil 1, Bestimmung der Flüssigkeitsaufnahme" is described in the detailed description of the invention, below.

By concentrating the absorbent material in the back half section of the absorbent article, urine is prevented from leaking from the product when used in the lying down position. As the back half section of the absorbent article is in a substantially horizontal position when used in a lying down position of the wearer, the majority of the liquids that are discharged in this position will under the influence of gravity and under influence of the weight of the user, be transported to the back half section.

When the core reaches its point of saturation, the relatively large amounts of liquids stored in the back of the absorbent core will result that liquid is squeezed out from the back transverse edge of the absorbent core. To prevent leakage of absorbed liquids from the perimeter of the core to the perimeter of the backsheet, the barrier means are located between the back transverse edge of the core and the waist transverse edge of the backsheet.

Another mechanism by which leakage can occur in the back half section, is via the topsheet of the absorbent article. To prevent leakage along the topsheet, the barrier means may be located on top of the absorbent core, in the back half section thereof. The advantage of such barrier structures is that liquids or other liquid or viscous waste is prevented from migrating along the topsheet to the back transverse edge of the absorbent core.

In one embodiment of an absorbent article according to the invention, the absorbent material may be solely comprised of hydrophilic fibers such as fluff pulp, rayon fibers or modified cellulosic fibers, or may be comprised of a foamed absorbent material as described in U.S. Pat. No. 5,268,224 (Desmarais). Applying more absorbent material of this kind in the back half section of the absorbent core can result in a so-called profiled core, which is of higher caliper in the back than in the front. Alternatively, the absorbent core is compressed to a uniform caliper, such that the density of the core is highest in the back area.

In a further embodiment of an absorbent article according to the invention, the absorbent material of the core comprises absorbent gelling material. The absorbent gelling material may be mixed with the fibrous or foamed material. Alternatively the absorbent core may be comprised of solely absorbent gelling material or may comprise layers of absorbent gelling material as described in European Application No 93309614.1.

Preferably the ratio of the average basis weight of the absorbent gelling material in the back half section and in the front half section is between 1.1 and 3, preferably between 1.2 and 3 and most preferably between 1.3 and 3.

The average basis weight of the absorbent gelling material in the front half section and in the back half section is determined by measuring the total weight of absorbent gelling material present in any one section and dividing this weight by the total area in which the absorbent gelling material is located. The weight of the absorbent gelling material is determined by separating the absorbent gelling material from the other absorbent material in any one section. The area where the absorbent gelling material is placed, is measured by applying a colouring agent to the absorbent core, such as bromocresol. The coloured areas are detected by visual inspection. Alternatively, the absorbent core may be exposed to x-rays to detect the quantity and location of the absorbent gelling material.

The barrier means may comprise a liquid-impermeable strip of material located underneath the topsheet. The strip overlies a part of the core along the back transverse edge of the core and is sealed in a liquid-tight manner to the backsheet along a sealing line.

Alternatively, the barrier means may comprise a liquid-impermeable sealing area, such as a line of connection between the topsheet and the backsheet located between the back transverse edge of the core and the back waist edge of the backsheet. The line of connection may be a glue line comprised of a single glue line, a spiral glue pattern as described in U.S. Pat. No. 4,098,632 (Sprague) or glue beads. Alternatively, the line of connection of topsheet and backsheet may be formed by fusion of the topsheet to the backsheet, for instance by crimping.

Again, alternatively, the barrier means comprises a stand-up barrier cuff having elastication means for spacing the distal edge of the cuff away from the topsheet. In again another embodiment, the barrier means comprise a section of the backsheet adjacent the back waist edge that is doubled-over to form a z-shaped fold.

The combination of the increased average basis capacity in the back half section of the absorbent core and the barrier means located in the proximity of the back waist region, make the absorbent article according to the invention especially adapted for bedridden users.

BRIEF DESCRIPTION OF THE DRAWINGS

The invention will be explained in detail with reference to the accompanying drawings. In the drawings:

FIGS. 2 to 5 show cross-sectional views of the core of the absorbent article of FIG. 1 along the longitudinal center line, FIG. 6 shows a front elevational view of an absorbent article comprising a backshield, FIG. 7 shows a cross-sectional view of the absorbent article of FIG. 6 along the longitudinal center line, FIG. 8 shows a front elevational view of an absorbent article comprising a stand-up barrier cuff, FIGS. 9 and 10 show a cross-sectional views of the absorbent article according to FIG. 8 along the longitudinal center line.

DETAILED DESCRIPTION OF THE INVENTION

Figure 1:
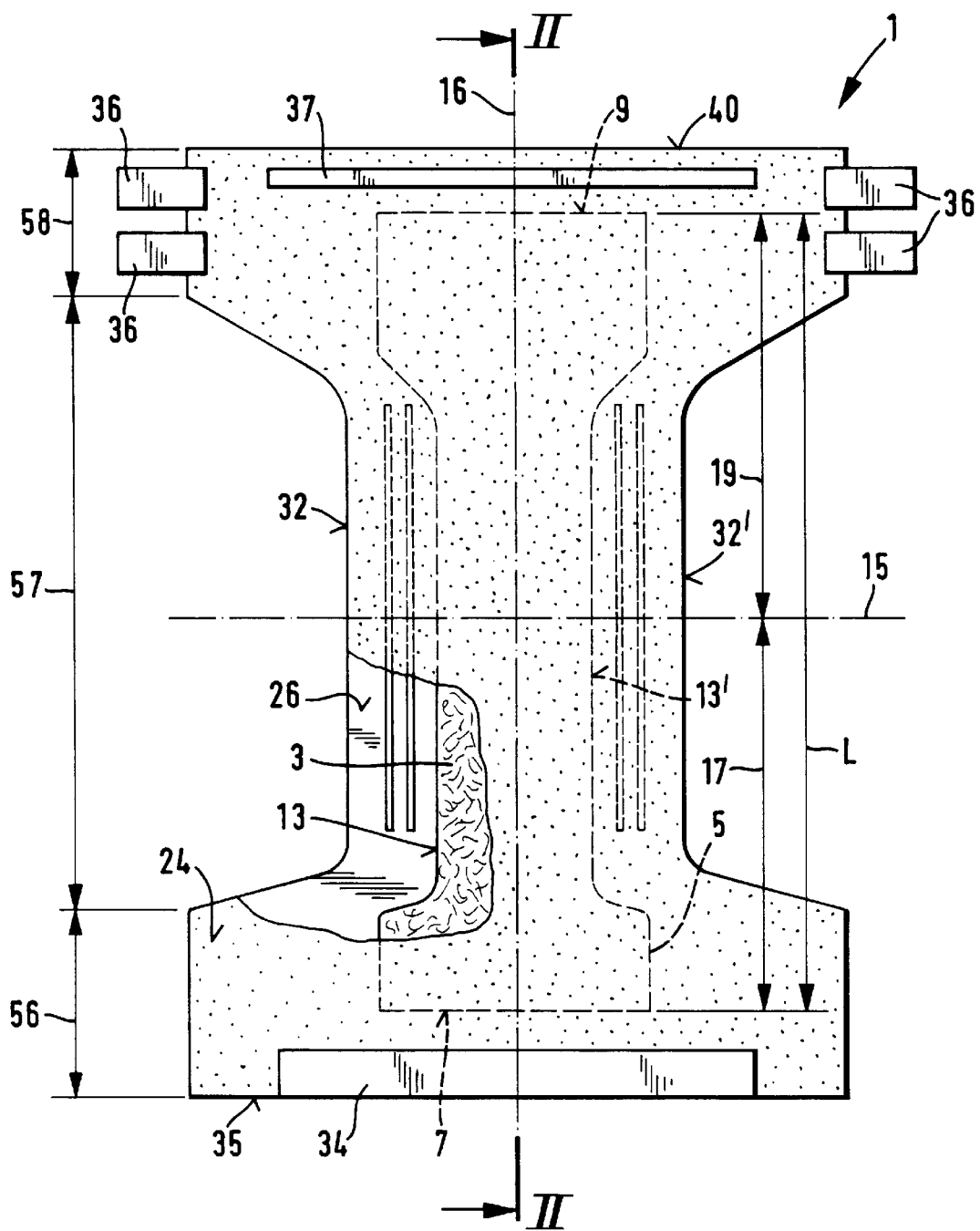
FIG. 1 shows a front elevational view of an absorbent article according to the invention.

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, or diaper as shown in FIG. 1. As used herein, the term "diaper" refers to an absorbent article generally worn by walking infants and incontinent persons that is worn about the lower torso of the wearer. In particular, the invention is related to an incontinence product, especially for adults, which product can absorb between 100 and 1000 ml of liquids, preferably between 300 and 1000 ml. It should be understood, however, that the present invention is also applicable to other absorbent articles such as incontinent briefs, incontinent undergarments, diaper holders and liners and the like.

FIG. 1 shows the absorbent article 1, comprising an absorbent core 3. The absorbent core 3 comprises a perimeter 5 having a front transverse edge 7, a back transverse edge 9 and two longitudinal sides 13,13'. An imaginary transverse center line 15 is located midway between the front transverse edge 7 and the back transverse edge 9 and divides the core 3 into a front half section 17 and a back half section 19.

In one embodiment of an absorbent article according to the invention, the amount of absorbent gelling material in the back half section 19 is larger than the amount of absorbent gelling material in the front half section 17. Preferably, the average amount of absorbent gelling material per unit area, or average basis weight, in the back half section 19 is higher than in the front half section 17.

Also the embodiments wherein the average basis weight of the fibrous or foamed absorbent material is higher in the back half section of the absorbent core 3, are within the scope of the invention. Preferably, the weight of the absorbent gelling material is higher in the back half section of the core 3.

In FIG. 1 the absorbent article, or diaper 1, is shown in its flat-out, uncontracted state (i.e., with elastic induced contraction pulled out) with portions of the article being cut-away to more clearly show the construction of the diaper 1 and with the portion of the diaper 1 which faces or contacts the wearer, the inner surface, oriented towards the viewer. As shown in FIG. 1, the diaper 1 preferably comprises a liquid pervious topsheet 24; a liquid impervious backsheet 26 joined with the topsheet 24; the absorbent structure, or core 3 being positioned between the topsheet 24 and the backsheet 26; elasticized leg cuffs 32, 32'; an elastic waist feature 34; and a fastening system generally multiply designated as 36.

The backsheet 26 comprises a front waist edge 35 and a back waist edge 40. Liquid barrier means 37 are located between the transverse centerline 15 of the core 3 and the back waist edge 40 of the backsheet, preferably between the back transverse edge 9 of the core 3 and the back waist edge 40 of the backsheet.

In the embodiment of FIG. 1, the topsheet 24 and the backsheet 26 have length and width dimensions generally larger than those of the absorbent core 3. The topsheet 24 and the backsheet 26 extend beyond the perimeter 5 of the absorbent core 3. While the topsheet 24, the backsheet 26, and the absorbent core 3 may be assembled in a variety of well known configurations, preferred diaper configurations are described generally in U.S. Pat. No. 3,860,003 entitled "Contractable Side Portions for Disposable Diaper" which issued to Kenneth B. Buell on Jan. 14, 1975; and U.S. patent application Ser. No. 07/715,152, allowed, "Absorbent Article With Dynamic Elastic Waist Feature Having A Predisposed Resilient Flexural Hinge", Kenneth B. Buell et al. filed Jun. 13, 1991; each of which is incorporated herein by reference.

The absorbent core 3 may be any absorbent means which is generally compressible, conformable, non-irritating to the wearer's skin, and capable of absorbing and retaining liquids such as urine and other certain body exudates. The absorbent core 3 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 3 should, however, be compatible with the design loading and the intended use of the diaper 1. In a preferred embodiment according to the invention, the absorbent core is intended for use by adults or juveniles and is able to absorb between 100 and 1000 ml of body fluids. Further, the size and absorbent capacity of the absorbent core 3 may be varied to accommodate wearers ranging from infants through adults. Exemplary absorbent structures for use as the absorbent core 3 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. Each of these patents are incorporated herein by reference. A preferred embodiment of the absorbent core 3 has longitudinal dimension, L, of about 60 cm, a back transverse edge 9 of about 30 cm, a front transverse edge 7 of 30 cm and a width along the transverse center line 15 of about 20 cm.

The backsheet 26 is positioned adjacent the garment surface of the absorbent core 3 and is preferably joined thereto by attachment means (not shown) such as those well known in the art. For example, the backsheet 26 may be secured to the absorbent core 3 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola et al. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 3 from wetting articles which contact the diaper 1 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mils). Particularly preferred materials for the backsheet include RR821 blown films and RR5475 cast films as manufactured by Tredegar Industries, Inc. of Terre Haute, Ind. The backsheet 26 is preferably embossed and/or matte finished to provide a more clothlike appearance. Further, the backsheet 26 may permit vapors to escape from the absorbent core 3 (i.e., breathable) while still preventing exudates from passing through the backsheet 26.

The topsheet 24 is positioned adjacent the body surface of the absorbent core 3 and is preferably joined thereto and to the backsheet 26 by attachment means (not shown) such as those well known in the art. Suitable attachment means are described with respect to joining the backsheet 26 to the absorbent core 3. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet 24 and the backsheet 26 are joined directly to each other in the diaper periphery and are indirectly joined together by directly joining them to the absorbent core 3 by the attachment means (not shown).

The topsheet 24 is compliant, soft feeling, and non-irritating to the wearer's skin. Further, the topsheet 24 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of a hydrophobic material to isolate the wearer's skin from liquids contained in the absorbent core 3. The hydrophobic material may have a hydrophilic coating. There are a number of manufacturing techniques which may be used to manufacture the topsheet 24. For example, the topsheet 24 may be a nonwoven web of fibers spunbonded, carded, wet-laid, meltblown, hydroentangled, combinations of the above, or the like. A preferred topsheet is carded and thermally bonded by means well known to those skilled in the fabrics art. A preferred topsheet comprises a web of staple length polypropylene fibers such as is manufactured by Veratec, Inc., a Division of International Paper Company, of Walpole, Mass. under the designation P-8.

The diaper 1 may also comprise elasticized leg cuffs 32,32' for providing improved containment of liquids and other body exudates. Each elasticized leg cuff 32 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 1, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff.

The diaper 1 preferably further comprises an elastic waist feature 34 that provides improved fit and containment. The elastic waist feature 34 is that portion or zone of the diaper 1 which is intended to elastically expand and contract to dynamically fit the wearer's waist. The elastic waist feature 34 at least extends longitudinally outwardly from at least one of the waist edges of the absorbent core 3 and generally forms at least a portion of one of the waist regions 56 or 58 of the diaper 1. Disposable diapers are generally constructed so as to have two elastic waist features, one positioned in the first waist region and one positioned in the second waist region, although diapers can be constructed with a single elastic waist feature. Further, while the elastic waist feature or any of its constituent elements can comprise a separate element affixed to the diaper 1, the elastic waist feature 34 is preferably constructed as an extension of other elements of the diaper such as the backsheet 26 or the topsheet 24, preferably both the backsheet 26 and the topsheet 24.

The elasticized waistband 34 may be constructed in a number of different configurations including those described in U.S. Pat. No. 4,515,595 issued to Kievit et al. on May 7, 1985 and the above referenced U.S. patent application Ser. No. 07/715,152; each of these references being incorporated herein by reference.

The diaper 1 also comprises a fastening system 36 which forms a side closure which maintains the first waist region 56 and the second waist region 58 in an overlapping configuration such that lateral tensions are maintained around the circumference of the diaper to maintain the diaper on the wearer. Exemplary fastening systems are disclosed in U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; and the hereinbefore referenced U.S. patent application Ser. No. 071715,152; each of which is incorporated herein by reference.

FIG. 2 shows a cross-sectional view of the core 3 along the longitudinal center line 16. Within the core 3, four sections 13a,13b,13c and 13d of equal length, L/4, can be considered, the caliper of the core being different in each section. In the embodiment of FIG. 2, the core 3 comprises fluff pulp of a uniform density. The caliper of section 13a is about 7 mm. The caliper in section 13b is about 10 mm, the caliper of section 13c is about 8 mm and the caliper in section 13d is about 5 mm. Hence the ratio of the basis weights of the fibers of combined sections 13a and 13b, which form the back half section of core 3, and combined sections 13c and 13d, which form the front half section, is about 1.3.

The core 13 may comprise cellulosic fibers, synthetic fibers such as crimped polyester fibers, mixtures of synthetic and cellulosic fibers or absorbent foam material as described in U.S. Pat. No. 5,268,224 (Desmarais). The caliper of the core 3 as shown if FIG. 2 can be made uniform by calendering. This is illustrated in FIG. 3. The core 3 of FIG. 3 comprises areas of relatively high density in the back half section 13a, 13b and a relatively low density in the front half section 13c,13d. The density of the fibrous or foamed absorbent material in the front and back half sections may range from 0.1 to 1 g/cm$^3$. The density in each section is proportional to the caliper before calendering to a uniform caliper. The increased density of the fibers in the back half section improves retention of liquids in that section as the smaller interfiber capillaries will exert a higher suction on liquids in the back half section.

The core 3 in FIGS. 4 and 5 comprises a water-insoluble, absorbent gelling material, which swells upon contact with liquids to form a hydrogel. Such materials are described in detail in U.S. Pat. No. Re. 32,649 (Brandt) and can absorb at least 20 times their own weight of liquid. The hydrogel material may be in particulate form, particle sizes ranging from 10 micrometers to 2000 micrometers or can come in the form of flakes, fibers or sheets. The hydrogel material may also be comprised of an interpartically crosslinked aggregate as described in U.S. Pat. No. 5,102,597 (Roe). The core 3 in FIG. 4 comprises a lower layer 63, which is substantially free of absorbent gelling material or which contains small size absorbent gelling material particles or absorbent gelling material fines, as described in EP-A-0 567 738 (Plischke). The lower layer 63 serves to contain the absorbent gelling material in the upper layer 64 and to prevent the absorbent gelling material particles from contacting the backsheet and hence cause surface irregularities on the backsheet (so called "pock marking") and to prevent the absorbent gelling material from perforating the backsheet.

In the absorbent core of FIG. 4, the absorbent gelling material is uniformly dispersed through the thickness, W, of each region 13a–13d of the layer 64. However, the absorbent gelling material may be present in different concentrations throughout the thickness of layer 64 of the core 3, and may be highest in the parts of the core that are furthest away from the wearer (those parts of layer 64 that are located closest to layer 63). Such cores with a so-called absorbent gelling material "gradient" are described in detail in EP-A-0 198 683 (Duenk).

In the embodiment of FIG. 4, the basis weight of the absorbent gelling material in section 13a is about 0.012 g/cm$^2$, the basis weight in section 13b being about 0.016 g/cm$^2$, the basis weight in section 13c being about 0.012 g/cm$^2$ and the basis weight in section 13d being about 0.008 g/cm$^2$ In a preferred embodiment, section 13a contains about 25%, and section 13b contains about 35% by weight of the total amount of absorbent gelling material present in the layer 64. Section 13c may contain about 25% and section 13d about 5% of the total weight of absorbent gelling material in layer 64.

Preferably, the absorbent gelling materials are "high gel strength" materials. High gel strength absorbent gelling material particles will undergo relatively little deformation upon being wetted such that the gelling material does not flow into the capillary void space of the fibrous material and causes undesired gel blocking. Suitable absorbent gelling materials have Gel Layer Permeability (GLP) values higher than $4 \times 10^{-7}$ cm$^3$/s/g. The GLP value can be measured by the method as described in European Application No. 93309614.1.

In the embodiment of FIG. 4, the basis weight of the fibrous or foamed absorbent material is equal for the sections 13a–13d in layer 64. The basis weight of the fibrous or foamed absorbent material may typically be about 0.05 g/m$^2$. However, in addition to a varying basis weight of the absorbent gelling material for each section 13a–13d, the basis weight of the fibrous or foamed absorbent material may also vary in each region 13a–13d,as shown in FIG. 5. Again, the core 3 as shown in FIG. 5 can be calendered to a uniform caliper.

FIG. 6 shows an embodiment of the absorbent article 1 wherein the barrier means 37 are formed by a strip of material 38, also referred to as "backshield". The strip 38 underlies the topsheet 24 along the back transverse edge 9 of the core 3. FIG. 7 shows a cross-sectional view of the article of FIG. 6 along the longitudinal centerline 16. The strip of material 38 is preferably of liquid-impervious material such as a polyethylene film, but can also be formed by a hydrophobic non-woven material. The strip 38 is connected to the backsheet 26 along a sealing line 42, which may be formed by a fusion bond, a glue line or spiral or an ultrasonic bond. The strip 38 prevents leakage from the back transverse edge 9 of the core to the back waist edge 40 of the backsheet 26. In an alternative embodiment, the strip 38 may be located on top of the topsheet 24.

FIG. 8 shows an absorbent article 1 wherein the barrier means 37 are formed by an elasticated stand-up barrier cuff 39. The barrier-cuff 39 comprises a strip of material 44 which may be liquid-impervious or may be formed by an air-pervious non-woven material, such as spunbonded polypropylene fibers. The barrier cuff 39 is with a proximal edge 41 sealingly connected to the absorbent article 1 along sealing line 42. The barrier cuff 39 is further connected to the article 1 in sealing areas 43,43'. The distal edge 45 of the barrier cuff 39 comprises an elastic material 46, which has for instance been applied to the distal edge in a pre-stretched manner. The contraction of the elastic material 46 spaces the distal edge 45 away from the topsheet 24. Inversion of the barrier cuff 39 is prevented by the sealing areas 43,43', which fix the sides of the cuff 39 against the absorbent article 1.

FIGS. 9 and 10 show cross-sectional views of the absorbent article of FIG. 8 along the longitudinal center line 16. The barrier cuff 39, as shown in FIG. 9, is located between the back transverse edge 9 of the core 3 and the back waist edge 40 of the backsheet 26. The proximal edge of the cuff 39 is sealingly connected to the backsheet. The cuff 39 not only prevents liquids from leaking from the back transverse edge 9 of the core 3 to the back waist edge 40 of the backsheet, but also form a barrier against liquid or solid waste migrating along the topsheet 24 to the back waist edge 40.

In the absorbent article of FIG. 10, the barrier cuff 39 is located on top of the topsheet 24. Although liquids stored in the core 3 can pass underneath the barrier cuff 39, the cuff 39 isolates the back waist edge 40 from liquid and solid waste which is not directly absorbed by the core, for instance large volumes of liquid that are very rapidly discharged, or viscous wastes which cannot be quickly taken up by the core 3. In addition to barrier cuff 39, an additional sealing line, or back waist shield may be located between the back waste edge 40 of the backsheet 26 and the back transverse edge 9 of the core 3.

Figure 11:
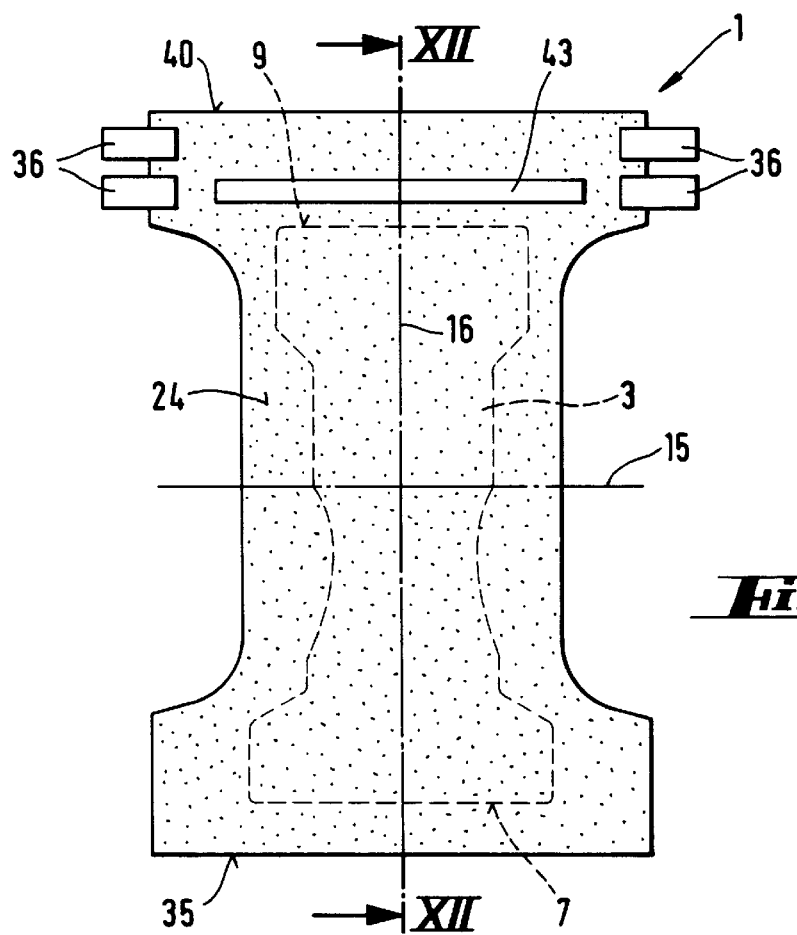
FIG. 11 shows a front elevational view of an absorbent article wherein the topsheet is connected to the backsheet in a sealing area.
Figure 12:
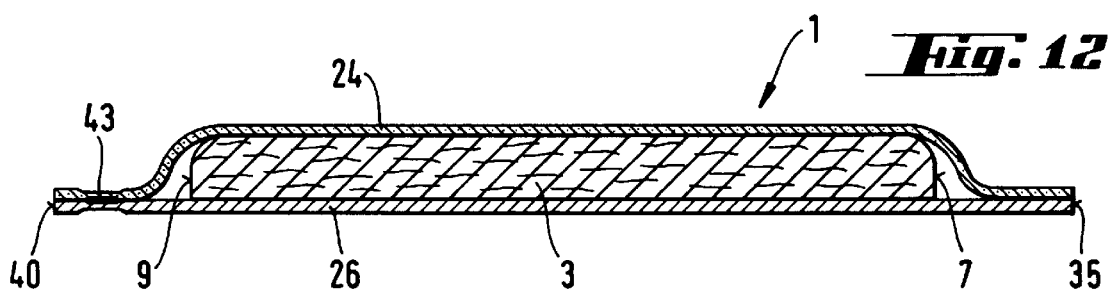
FIGS. 12 and 13 show cross-sectional views of the absorbent article of FIG. 11 along the longitudinal center line.
Figure 13:
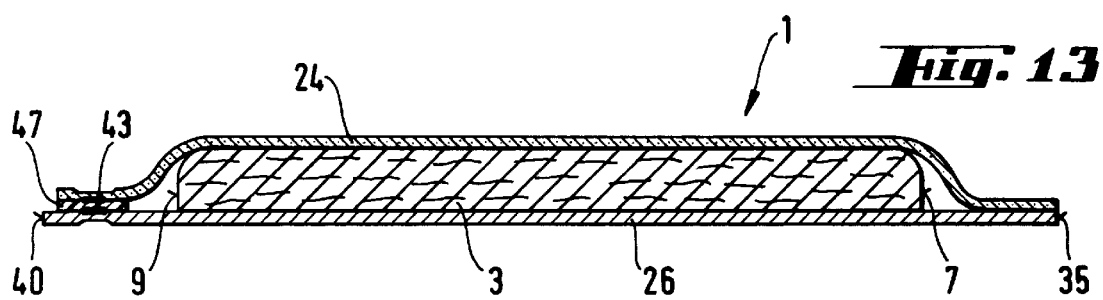

In the absorbent article of FIG. 11, the barrier means 37 are formed by sealing area 43 in which the topsheet 24 is sealed to the backsheet 26 in a liquid-tight manner. As shown in FIG. 12, the barrier means comprise an area 43 wherein the topsheet 24 is fused to the backsheet 26 by crimping. Alternatively, an elastic waistband 47 may be comprised in the barrier means, the topsheet 24 being connected to backsheet 26 via the elastic waistband 47. This is shown in FIG. 13.

Figure 14:
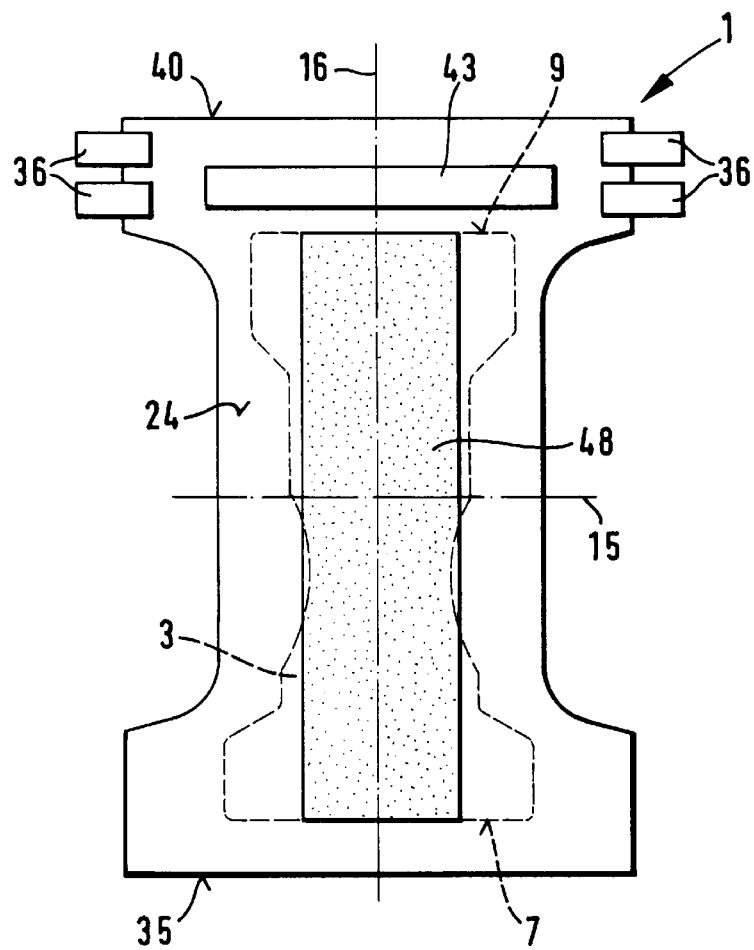
FIG. 14 shows a front elevational view of an absorbent article having a topsheet comprising a liquid-impervious area.

FIG. 14 shows an absorbent article wherein the topsheet 24 comprises a liquid-pervious area 48 located over the absorbent core 3 which has been indicated by shading. Outside the area 48, the topsheet is liquid-impervious and is connected to the backsheet 26 along the topsheet's periphery. In addition to the sealing connection of the periphery of the topsheet 24 to the periphery of the backsheet 26, a sealing area 43 may be comprised between the back transverse edge 9 and the back waist edge 40, although this sealing area can be omitted. The topsheet may be comprised of a film or a laminate of fibers and film and may be partially perforated in the central area 48. Suitable material for such a topsheet is for instance a topsheet as used in ALWAYS pantiliners, made by the Procter & Gamble Company. Alternatively, a hydrophobic or liquid-impervious coating may be applied to the inner or the outer surface of the topsheet 24 outside the liquid-pervious areas 48.

Figure 15:
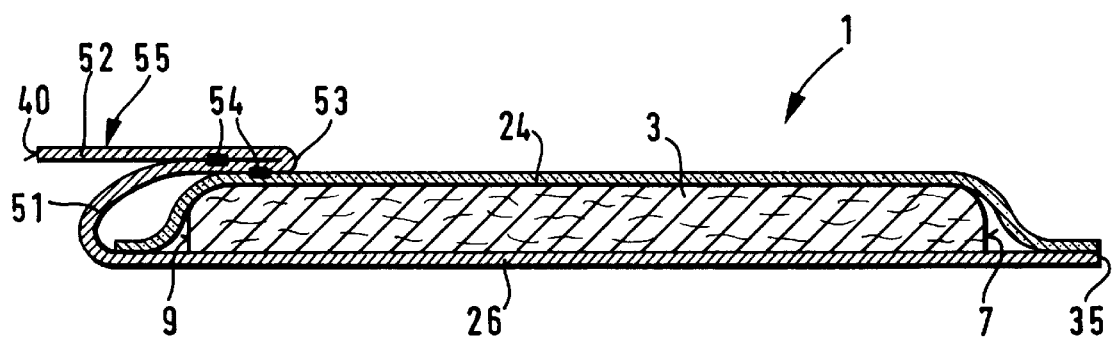
FIG. 15 shows a partial cross-sectional view of an absorbent article having a folded waist section as barrier means.

FIG. 15 shows an embodiment wherein a back waist section of the backsheet 26 is doubled over in an inward z-fold 55. The back waist section comprises a first section 51 which is folded inwardly onto the topsheet 24 and is attached to the topsheet by fixing means 54 which may be ultrasonic joint, fusion spot-bonds or an adhesive connection. The back waist section 52 of the backsheet 26 is folded outwardly along a foldline 53 and is glued in a doubled-over position onto the section 51.

Figure 16:
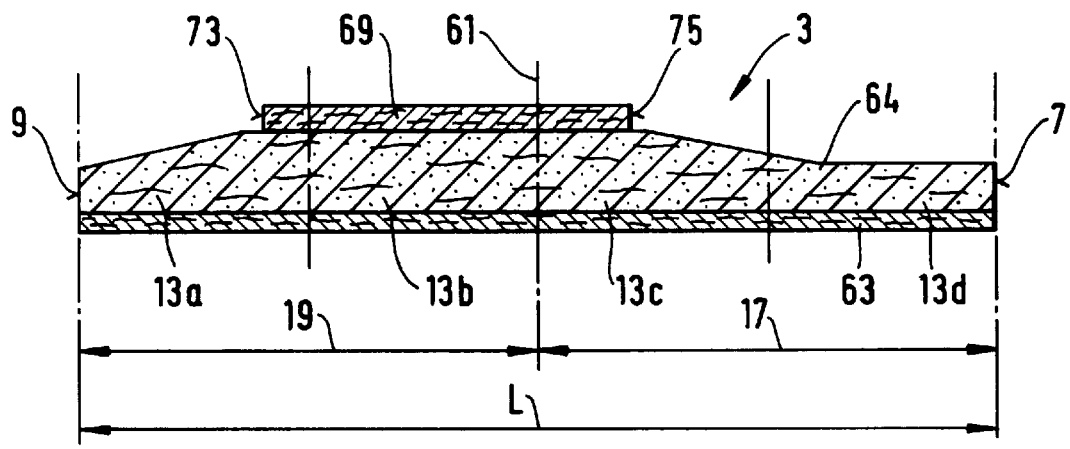
FIGS. 16 and 17 show cross-sectional views along the longitudinal center line of the core of the absorbent article according to the invention, the core comprising an acquisition/distribution layer, FIG. 18 schematically shows the region of the absorbent core for measuring the average basis capacity of the core, FIG. 19 schematically shows the test equipment for measuring the average basis capacity of an absorbent structure and FIGS. 20 and 20a schematically show the test equipment for determining the run-off of liquid via the back transverse edge of the core.

In FIG. 16 an embodiment of an absorbent core 3 is shown that comprises an acquisition/distribution layer 69, located on top of the layer 64 of core 3. The acquisition/distribution layer serves to quickly collect large gushes of liquids and to isolate these from the body of the wearer until these liquids have been absorbed in the underlying layer 64. The density of the acquisition/distribution layer is preferably between 0.03 and 0.13 g/cm$^3$ the basis weight being between 100 and 500 g/m$^2$, depending on the volume of the gush that is to be taken up. A preferred material for the acquisition/distribution layer 69 is chemically stiffened cellulose material as described in EP-A-0 429 112 (Herron) U.S. Pat. Nos. 4,898,642 (Moore) and 4,889,597 (Bourbon). Further useful acquisition/distribution layers comprise open networks of thermally bonded synthetic fibers as described in U.S. application Ser. No. 08/141,156 and EP-A-513 148.

An important property of the acquisition/distribution layer 69 is its ability to maintain a sufficient void volume for liquid uptake, even when wet. The fibers in the layer 69 should be sufficiently resilient to not collapse in their wet state upon compression. It was found that layers having a wet compressibility of at least 5 cm$^3$g$^{-1}$ and a drip capacity of at least 10 g g$^{-1}$ can be successfully used in acquisition/distribution layer 69.

The wet compressibility and the drip capacity can be measured by the test described below. All tests are carried out at about 23±2_C and at 50±10% relative humidity. The specific synthetic urine used in the test methods is commonly known as Jayco SynUrine and is available from Jayco Pharmaceuticals Company of Camp Hill, Pa. The formula for the synthetic urine is: 2.0 g/: of KCl; 2.0 g/l of Na$_2$SO$_4$; 0.85 g/l of (NH$_4$)H$_2$PO$_4$; 0.15 g/l (NH$_4$)H$_2$PO$_4$; 0.19 g/l of CaCl$_2$; ad 0.23 g/l of MgCl$_2$. All of the chemicals are of reagent grade. The pH of the synthetic Urine is in the range of 6.0 to 6.4.

Sample Pad Preparation for Wet Compressibility and Drip Capacity Tests

The sample pads are prepared using a padmaker machine of type such as is described below or an equivalent machine, which provides a consistent and homogeneous laydown of fluff. Four 30 g portions of dry fluff (or equivalent material, for example chemically cross-linked cellulose) are weighed out. A ply of tissue porous enough for air to pass through it while retaining fluff on it, is cut to 36.8 cm×36.8 cm (14.5"×14.5"), and is placed evenly on a forming screen of an air laid felt padmaker machine. The tissue completely covers the forming screen and is made to curve up at its sides to prevent escape of the fluff. The tissue forms the bottom of the pad. The vacuum chamber motor and compressed air supply on the padmaker machine are turned on. One 30 g portion of fluff is added to the sample chamber on the padmaker machine in small amounts via a sample feed and without obstructing the blades of the machine. Compressed air is circulated vigorously in the chamber to expedite separation and passage of the fibres through a plexiglass cylinder and the prismoid column to the forming screen.

The vacuum is turned off and the forming screen is pulled out of the padmaker machine and rotated through a quarter turn in the clockwise direction. The screen is returned to the padmaker machine. Another 30 g portion of fluff is added to the chamber on the machine and the above procedure is repeated. Fluff is added in the same manner until all four portions have been transferred to the forming screen. The forming screen, and the pad formed thereon, is then removed from the padmaker machine, and the pad is carefully transferred from the screen to a piece of cardboard, or similar smooth flat surface. A second ply of tissue is added to the top of the pad, and a second piece of cardboard placed on top of that.

A steel weight having dimensions of around 35.6 cm×35.6 cm×2.5 cm (14"×14"×1") having a weight of around 16.3 kg (36 lbs) is placed on top of the pad for approximately 120 seconds, or longer until the pad is needed. The weight is then removed and the pad is pressed by application of a force of around 4,500 kg (10,000 lbs) on a large Carver press to improve pad integrity. The pad is removed from the press and trimmed on a paper cutter to have dimensions around 30.5 cm×30.5 cm (12"×12"), and is then further cut according to the size required by the particular test in which it is to be used.

The use of a padmaker machine to form the sample pads is not intended to be limiting. Any suitable method can be used provided a consistent and homogeneous laydown of fluff is achieved, which is then compressed under the above conditions to give a pad having substantially the same density and basis weight as achieved above.

Wet Compressibility Test

This test is designed to measure the volume of a pad of fibrous material under varying load conditions when wet. The objective is to measure the fibrous material's resistance to load by measuring the volume maintained under that load.

A fluff test pad is prepared as described above. Any tissue present on the surfaces of the pad is removed. The pad is then densified under a 3.6 kg cm$^{-2}$ (51 psi) load for pad integrity reasons using a Carver laboratory press. The thickness of the pad is measured and its fibre density calculated by pad weight÷(pad thickness×pad area).

The dry weight of the pad is multiplied by 10, and this represents the target wet weight on loading. The dry pad is transferred onto a top loading balance having a 0.01 g sensitivity. Synthetic urine is dispensed slowly onto the pad until the target wet weight is achieved as measured by the balance. The wet pad is carefully transferred onto the surface of a compressibility tester of the Buckeye design, and a weight having substantially the same area as the pad (about 10.2 cm×10.2 cm) and corresponding to a pressure of 77 g cm$^{-2}$ (1.1 psi) is lowered slowly onto the pad. The pad is left for 60 seconds to allow it to equilibrate under the load, and then the thickness of the compressed pad is recorded using calipers.

The Wet Compressibility is the void volume per gram of dry fluff and is calculated as follows:

Void Volume (cm$^3$)=Total Volume–Fibre Volume=(pad thickness under load (cm)×pad area (cm$^2$))–(pad dry weight (g)/fibre density (g cm$^3$)

Wet Compressibility=Void volume per gram=[(pad thickness under load (cm)×pad area (cm$^2$))–(pad dry wt. (g)/fibre density (g cm$^{-3}$)]÷pad dry wt. (g)

where fibre density is calculated from the initial pad weight and thickness measurements (i.e. under no load conditions).

Drip Capacity Test

A sample pad prepared as described above is cut on a paper cutter to have dimensions 7.5 cm×7.5 cm. The pad is weighed and is placed on a large mesh wire screen which is in turn positioned on a drip tray. The whole apparatus is then mounted on a top-loading balance.

Synthetic urine is introduced via a pump (Model 7520-00, as supplied by Cole-Parmer Instruments Company, Chicago, USA) into the centre of the sample pad at a rate of 5±0.25 ml s$^{-1}$. The time for the pad to release the first drop of synthetic urine through the bottom of the pad and into the drip tray is recorded. The pump is immediately stopped as soon as this occurs. The time recorded and the pumping rate are then used to calculate the volume (ml) of synthetic urine absorbed by the sample on reaching saturation, i.e. when the sample starts to drip. The balance can be used to check this periodically, thereby minimising any variation in the pump delivering the synthetic urine. This is known as the Drip Capacity, and is given as the ratio:

{Urine retained by sample pad on saturation (ml)}/{Dry Weight of sample (g)}

Figure 17:
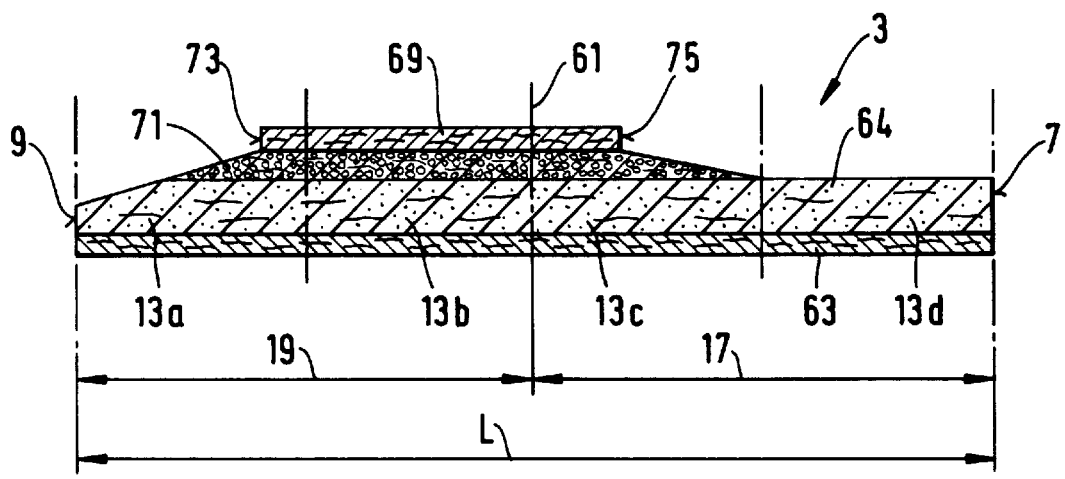

In the embodiment of FIGS. 16 and 17, the acquisition/distribution layer 69 is of generally rectangular shape and comprises a back edge 73 and a front edge 75. The distance between the back edge 73 of the acquisition/distribution layer 69 and the cross sectional center line 61 is larger than the distance between the front edge 75 and the cross-sectional center line. For irregularly shaped acquisition/distribution layers 69, the surface area of the part of the acquisition/distribution layer 69 located between the transverse center line 15 and the back edge 9 of the core 3 is larger than the surface area of the acquisition/distribution layer 69 located between the transverse center line 15 and the front edge 7 of the core 3. Preferably the ratio of the total weight of absorbent material in the acquisition/distribution layer located in the back half section of the absorbent core 3 and located in the front half section of the acquisition-distribution layer is between 1.1 to 3.

In the embodiment of FIG. 17, an extra layer 71 of absorbent gelling material is located underneath the acquisition/distribution layer 69. This layer of absorbent gelling material serves to quickly drain the layer 69, such that it is ready for subsequent gushes of liquid, and maintains a dry buffer adjacent the skin of the wearer.

Absorbent gelling materials of high gel strength as mentioned above are suitable to use in the layer 71, as they maintain a relatively open structure through which liquids can pass to the underlying layer 64 without adverse effects of gel blocking. The absorbent gelling material in layer 71 may be mixed with the fibers in the upper part of the layer 64, and may be introduced in this layer during the airlaying of the fibers of the layer 64, using a powder spray nozzle as described in EP-B-0 330 675.

Alternatively, the layer 71 contains a layer of absorbent gelling material which is not substantially mixed with the fibrous or foamed absorbent material of the layer 64. Such a layer of absorbent gelling material may be bonded to a tissue by means of adhesive or frictional forces, as disclosed in U.S. Pat. No. 4,600,458 (Kramer) or may contain a single layer of loose absorbent gelling material particles. Alternatively, the layer 71 comprises a layer of interparticle-crosslinked particles which form a porous macroscopic aggregate as described in U.S. Pat. Nos. 5,102,597 (Roe) and 5,180,622 (Berg).

When the layers 71 contain a substantially pure layer of absorbent gelling material, it is important that the layer 71 remains permeable for liquids. It was found that absorbent gelling materials having a Gel Layer Permeability of at least 4×10$^{-7}$ cm$^3$/s/g can advantageously be used in the layer 71. The GLP value is an indication of the ability of the absorbent gelling material to maintain a permeable structure and to allow liquid transport through the absorbent gelling material layer, even when wet. The test for measuring the GLP values has been described in detail in European application no. 93309614.1. Alternatively, the absorbent gelling material has an absorption against pressure value (AAP) of at least 23 g/g at a confining pressure of 5 kPa (0.7 psi). A test for measuring the AAP-values has been described in European patent application no. 93909614.1.

For determining the weight of absorbent gelling material in the embodiment of FIG. 17, in the front half and back half sections 17 and 19, the total weight of absorbent gelling material in each section comprises the absorbent gelling material present in both layers 71 and 64. The regions 13a and 13b each contain about 20% by weight the absorbent gelling material in the core 3, regions 13c and 13d each contain 15% by weight and layer 71 contains 30% of the total weight of absorbent gelling material in layers 64 and 71. The absorbent gelling material in the layer 71 need not have the same chemical or physical or physical properties as the absorbent gelling material in the layer 64, but can for instance have a slower absorption speed or a lower absorption under pressure.

In the following example, the rewet properties of a product having an absorbent core comprising a back half section having a high average basis capacity will be determined and will be compared with the rewet properties of similar products which do not have a majority of the absorbent gelling material located in the back half section. Thereafter, the effect of the liquid barrier means will be measured in a run-off test. The determination of the average basis capacity, the rewet test and the run-off test are described here below:

Average Basis Capacity

Figure 18:
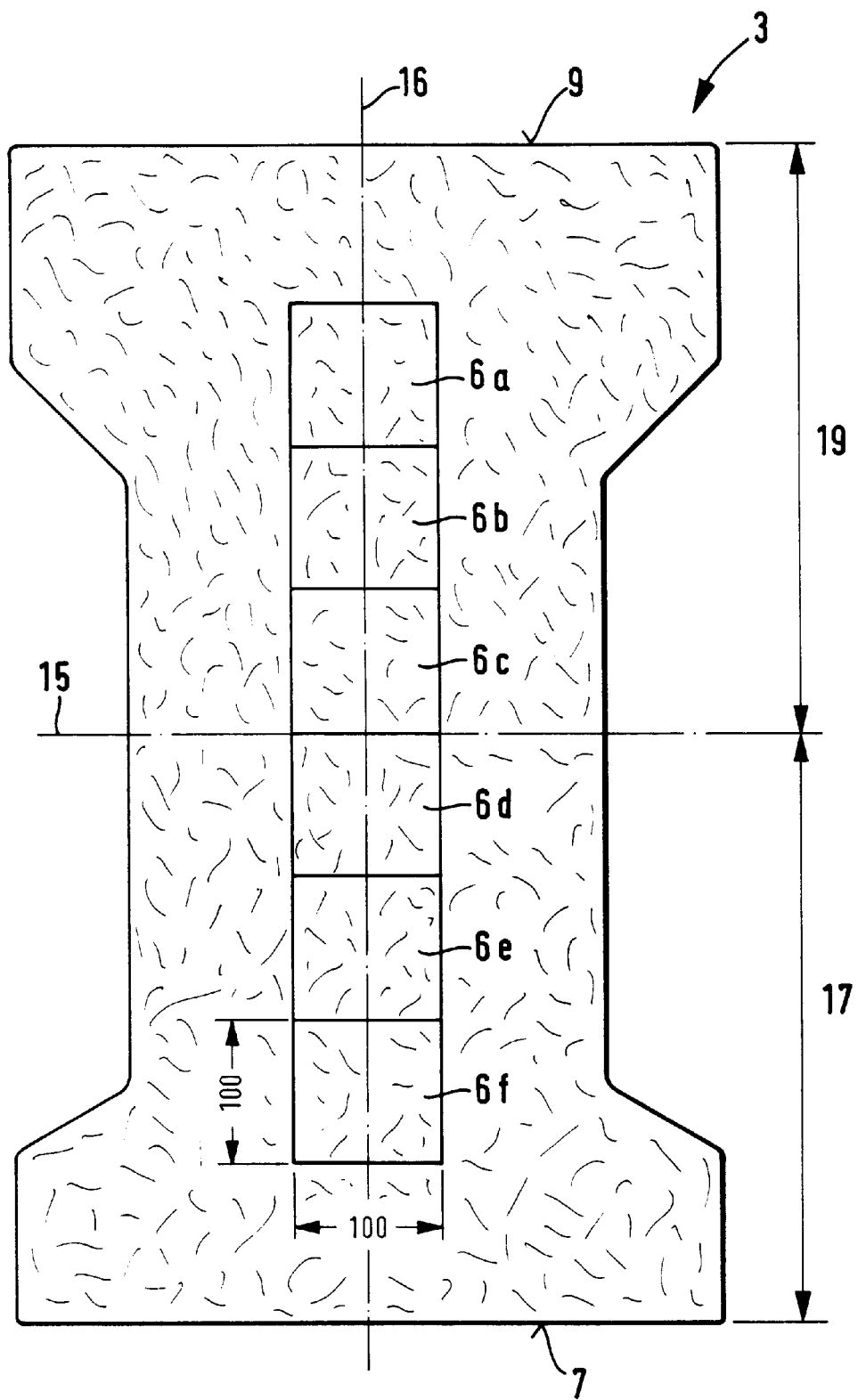

The average basis capacity test measures the amounts of liquid absorbed per gram of absorbent material in the central area 6a–6f of the absorbent core, as indicated in FIG. 18.

First the average basis weight of the material in the central area 6a–6f is determined in accordance with "Prüfmethode Nr. 1/93 MDS-HI Teil 1; Bestimmung der Fl üssigkeitsaufnahme". The absorbent product is laid flat on a surface and the transverse center line 15 that is located midway between the front transverse edge 7 and the back transverse edge 9 and that divides the absorbent core into the front half section 17 and back half section 19, is marked. Likewise the longitudinal center line 16 is marked. A total of up to six test samples 6a–6f each of 100×100 mm size are labelled and cut out of the absorbent product as detailed in FIG. 18. In case of smaller product size, the number of samples can be reduced. In any case, the samples are taken symmetrically around the transverse center line 15.

Typically each sample 6a–6f will be composed of absorbent material located between and contained by a nonwoven topsheet 24 and a water impervious backsheet 26 or outer material. The samples 6a–6f are symmetrically removed about the transverse center line above and below the transverse center line. The labelled samples are removed with the aid of a die or laboratory cutter and are weighed with a laboratory balance to an accuracy of 0.05 gram. For each sample the dry weight, $W_i$, is recorded.

Figure 19:
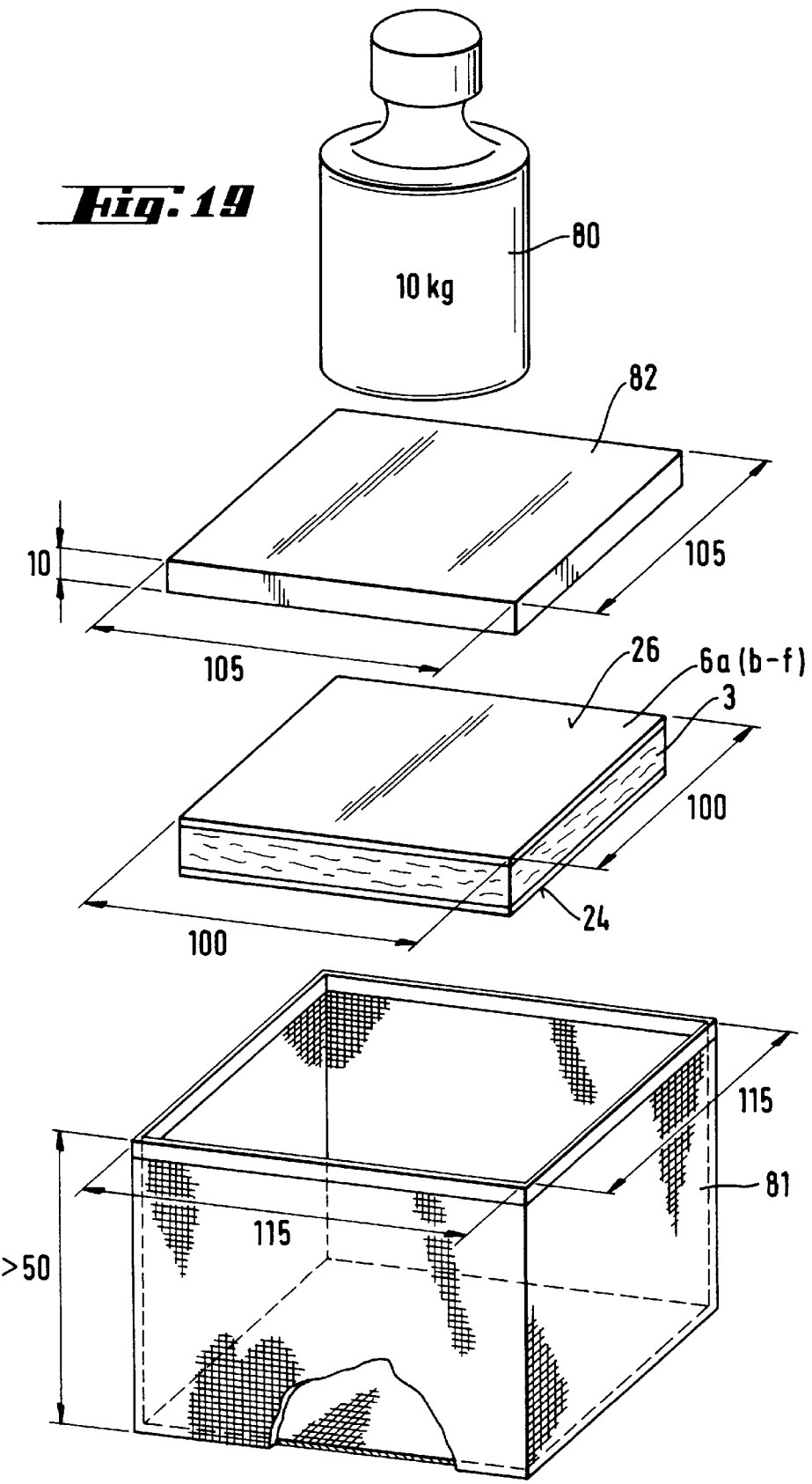

The samples are placed, one at a time, in a metallic meshed basket 81 as illustrated in FIG. 19 with the water impervious backsheet 26 or backing material placed upwards. A perspex plate 82 is placed on top of the sample and the metallic meshed basket 81 is submerged in Jayco synthetic urine which so that the sample and perspex plate 82 are fully submerged for a period of 20 minutes. After 20 minutes, the basket containing the sample is immediately removed and placed on a stand that allows excess test solution to readily drain away. Immediately a 10 kg weight is placed on top of the perspex plate lying on top of the sample for a period of 2 minutes such that a pressure of 100 g/cm$^2$ is exerted on the sample. After the 2 minutes the weight and perspex plate are immediately removed and the sample is immediately weighed. The weight of each sample loaded with liquid, $Wl_i$ is recorded.

The average basis capacity (g/g) for the front half section is given by:

$$1/3 \sum_i [(Wl_i - W_i)/W_i] \quad \text{[for samples } i = 6d, 6e, 6f\text{]}$$

Similarly, the average basis capacity can be determined for the back half section on the basis of samples 6a, 6b and 6c.

Rewet Test

In the rewet test the ability of an absorbent product to retain absorbed liquids inside the core, is measured. In the rewet test, an absorbent diaper is selected, weighed and the elastic components are either cut in half or removed to allow the product to be laid out in its flattened position. Front and back loading points for application of a test solution are clearly marked on the absorbent product. The front loading point is located on the longitudinal center line 16 at a distance 10 cm from the front transverse edge 7 inwards towards the transverse center line 15. The back loading point is located on the longitudinal center line 16 at a distance 15 cm from the back transverse edge 9 inwards towards the transverse center line 15.

In separate tests, either the front or the back loading point is selected and a volume typical of in in-use conditions of 240 ml of Jayco synthetic urine, of chemical composition as described in the text above, is dripped onto the loading point at a rate of 17 ml/sec.

A circular weight of 10 Kg and having a diameter of 16 cm and exerting a loading pressure of 50 g/cm$^2$ (0.7 psi), is placed onto the center of the loading point for a period of 30 minutes. After 30 minutes the weight is carefully removed and dried and eight (8) layers of pre-weighed filter papers (Eaton Dikeman 631, Nr 5) are immediately placed central onto the loading point and the weight gently lowered, without delay, onto the filter paper for exactly 30 seconds. The weight and filter paper are immediately removed on completion of the 30 seconds and the difference in filter paper weight is recorded as the first rewet value. A second set of eight (8) layers of pre-weighed filter papers are immediately placed central onto the loading point and the weight gently lowered, without delay, onto the filter paper for exactly 30 seconds. The weight and filter paper are immediately removed on completion of the 30 seconds and the difference in filter paper weight is recorded as the second rewet value. The total rewet is the sum of the two individual rewet values, i.e. rewet=1st+2nd rewet values.

Run-off Test

The run-off test method is utilised to test the effectiveness of a barrier means such as a backshield 38 as shown in FIGS. 7 and 8. The test simulates in use conditions typical for incontinence sufferers in a night time or lying situation where the absorbent material located in the back half of the product under either a large or repeated loading(s) becomes saturated potentially leading to leakage. The mechanism of such leakage can be either through pressure extrusion (via body movement) or simple capillary action whereby urine not adequately restrained within the core region is absorbed by the users clothing or bedding.

Figure 20:
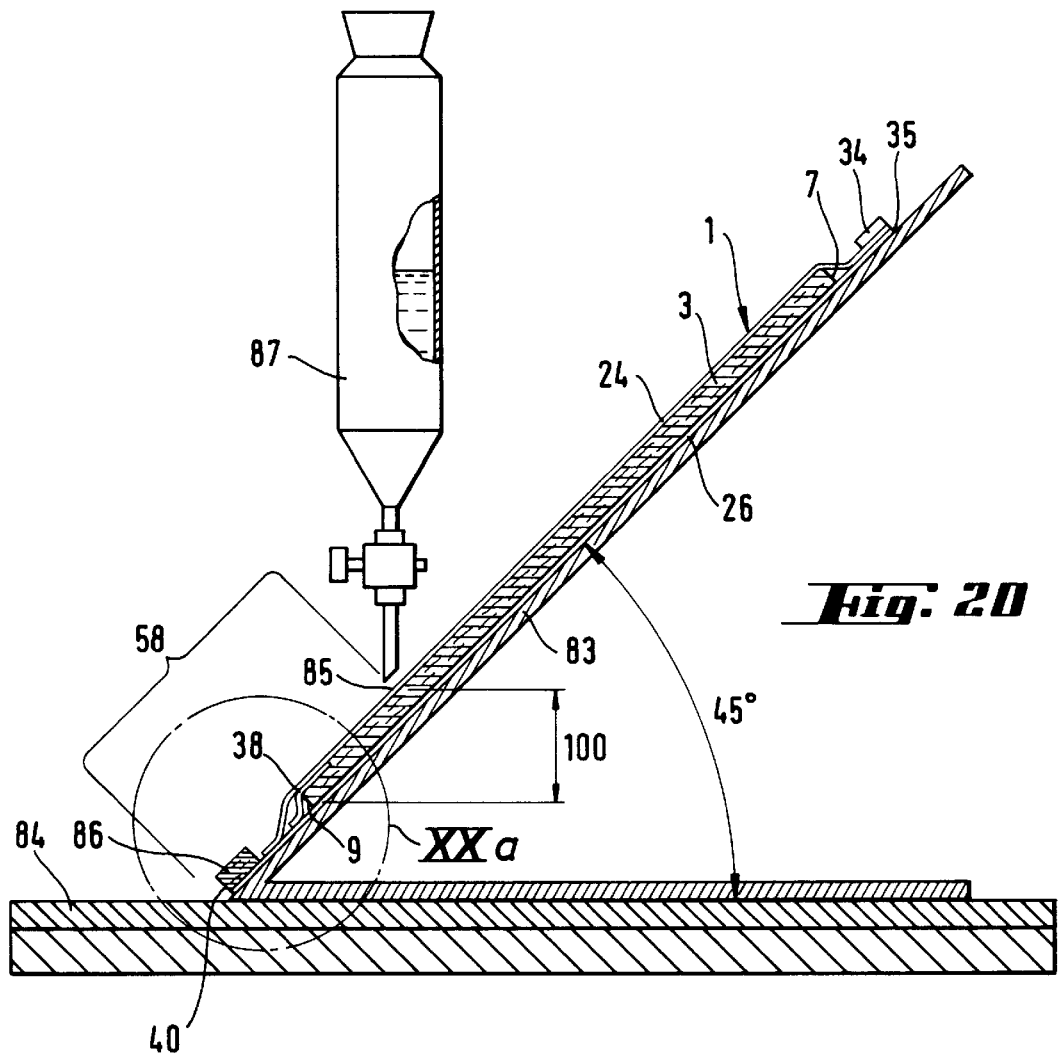
Figure 20A:
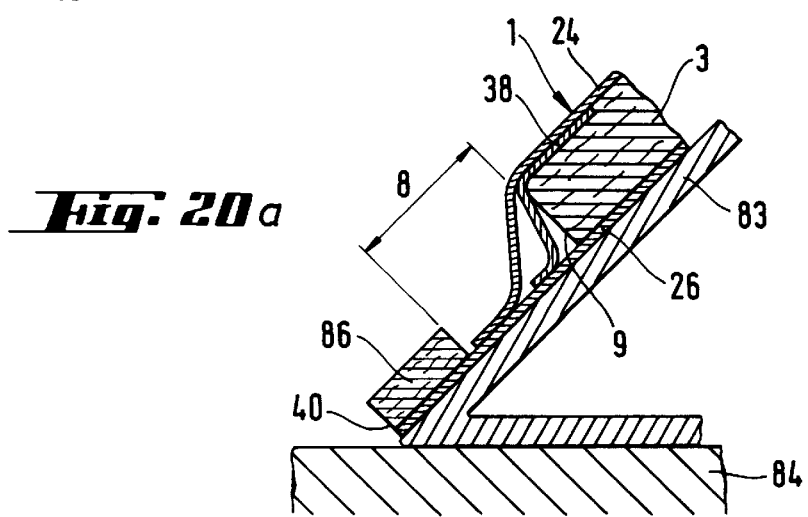

The test is performed using an apparatus as detailed in FIG. 20. The absorbent product is selected and the leg elastics are either cut or removed to facilitate flat placement of the product on a working surface. The loading point 85, located along the product's longitudinal center line 16 at a distance of 10 cm from the back transverse edge 9 of the core 3, is marked on the absorbent product.

The absorbent test product 1 is then laid flat and clamped onto a support 83 which is mounted on an adjustable height platform 84 at an angle of 45% to the platform 84. A stack 86 of 10 sheets of doubled over (150 cm×12.5 cm) BOUNTY tissues, manufactured by The Procter & Gamble Company, weighing about 37 grams, is placed in the back waist region 58 of the absorbent product 1 at a distance of 8 mm from the back transverse edge 9 of the core 3. A volume of 250 ml of Jayco Synthetic Urine of composition as detailed above, is added to a dispensing flask 87. The full 250 ml volume of synthetic urine is dispensed onto the test product from a height of 5 mm above the loading point 85 at a rate of 40 ml/min so as to simulate a single heavy loading gush.

Synthetic urine not adequately acquired and absorbed in the time available by the absorbent core 3 is typically extruded under the combined force of gravity and/or through capillary action and is collected by the stack of absorbent towels 86 or is contained by the waist shield 38. The tissues 86 are weighed both prior to and after an elapsed time period of 5 minutes following the cessation of the gush. The difference is recorded as run-off.

Comparative Example I

In this example three incontinence briefs, or diapers, were wetted in the front and back half sections and the rewet values were measured in each section. The average basis capacity of the back half section and the front half section of each sample was determined by the method described above. The samples are similar in terms of their dimensions and capacity and are representative of absorbent products typically in use for adult heavy incontinence sufferers. The following three products are compared:

1) An incontinence brief having an absorbent core according to the invention, for the user size group 'Medium'.
2) A incontinence brief otherwise identical to 1) but with a absorbent core comprising more absorbent gelling material in the front half section than in the back half section, and
3) A commercially available incontinence brief sold under the trade name Tena Slip Super (Art. No. 711200, manufacturer Mölnlycke AB) in the user size group 'Medium'.

Results of the rewet test and absorbent capacity measurements of the above products are given in Table I below.

From Table I it can be seen that for sample 1, which has in the back half section a larger amount of absorbent gelling material and a higher average basis capacity, the rewet in the back half section is smaller by about a factor 10 compared to the rewet of samples 2 and 3. Because of the low rewet values in the back half section, the samples 1 are especially adapted for use by bedridden users. In the lying down position, the liquid will be stored predominantly in the back half section of the core. Maintaining the rewet at an as low as possible level is especially important with bedridden users to avoid a negative impact on the skin of wetness and pressures which normally occur with incontinent bedridden users.

TABLE I

Comparison of the average basis capacity and rewet values in the front half section and back half section for three adult incontinence products.

| Parameter | Sample 1 Absorbent gelling material predominately in back half section | Sample 2 Absorbent gelling material predominately in front half section | Sample 3 Commercially available product |
| --- | --- | --- | --- |
| Product Dimensions | | | |
| Product Length (mm) | 838 | 838 | 805 |
| Product Width front (mm) | 625 | 625 | 650 |
| Product Width back (mm) | 637 | 637 | 634 |
| Absorbent Structure | | | |
| Core Length (mm) | 651 | 651 | 636 |
| Core width Center (15) (mm) | 200 | 200 | 175 |
| Core Width Back (9) (mm) | 325 | 325 | 330 |
| Core Width Front (7) (mm) | 325 | 325 | 325 |
| Total Core Area (sqcm) | 1597 | 1597 | 1580 (±60) |
| Total Core Weight (g) | 103 | 103 | 110 (±5) |
| Front Half Section | | | |
| Airfelt/Fibrous Material | | | |
| Area (sqcm) | 764 | 764 | 754 (±50) |
| Weight (g) | 43.5 | 43.5 | 46 (±3) |
| Basis Weigh (g/sqcm) | 0.056 | 0.056 | 0.062 |
| Absorbent Gel Material | | | |
| Area (sqcm) | 495 | 495 | 754 |
| Weight (g) | 4.5 | 7.5 | 6 (±0.5) |
| Basis Weigh (g/sqcm) | 0.0091 | 0.015 | 0.008 |
| Test Results Front Half | | | |
| Average Basis Capacity (g/g) | 9.2 | 10.9 | 8.6 |
| Rewet (g) | 1.6 | 0.19 | 2.7 |
| Back Half Section | | | |
| Airfelt/Fibrous Material | | | |
| Area (sqcm) | 833 | 833 | 826 |
| Weight (g) | 47.5 | 47.5 | 51 (±3) |
| Basis Weigh (g/sqcm) | 0.056 | 0.056 | 0.062 |
| Absorbent Gel Material | | | |
| Area (sqcm) | 495 | 495 | 826 |
| Weight (g) | 7.5 | 4.5 | 6 (±0.5) |
| Basis Weight (g/sqcm) | 0.015 | 0.091 | 0.0073 |
| Test Results Back Half | | | |
| Average Basis Capacity (g/g) | 10.9 | 9.2 | 8.6 |
| Rewet (g) | 0.17 | 1.6 | 2.8 |

Comparative Example II

In the following comparative example, three products indicated in Table II as sample 4, sample 5 and sample 6, are compared. Sample 4 is a product similar to sample 1 in the first comparative example, but is provided with liquid barrier means of the type depicted in FIG. 7. Sample 5 is a product identical to sample 1 in comparative example I and sample 6 is a product identical to sample 3 in comparative example I. From table II it can be seen for sample 5 the liquid run-off is reduced by about a factor 2 compared to the liquid run-off of sample 6. This is caused by the presence of an increased amount of absorbent material in the back half section of sample 5. However, the amount of absorbent gelling material cannot be increased at will, as at higher concentrations gel blocking will occur. Also for cost reasons, the amount of absorbent gelling material in the back half section cannot be increased at will. Hence liquid run-off cannot be completely prevented by increasing the amount of absorbent geling material in the back half section. As shown by sample 4, the addition of a liquid barrier means can further reduce the run-off to a negligible level. Reduction of the run-off, or leakage at the back waist section of the absorbent product is especially important for those products that are used by bedridden patients, for whom the combination of pressure and wetness can lead to a detrimental skin condition.

TABLE II

Comparison of the run-off values for three adult incontinence products.

| Parameter | Sample 4 Absorbent gelling material predominately in back half section with waistshield | Sample 5 Absorbent gelling material predominately in back half section without waistshield | Sample 6 Commercially available product without waistshield |
|---|---|---|---|
| Product Dimensions | | | |
| Product Length (mm) | 838 | 838 | 805 |
| Product Width front (mm) | 625 | 625 | 650 |
| Product Width back (mm) | 637 | 637 | 634 |
| Absorbent Structure | | | |
| Core Length (mm) | 651 | 651 | 636 |
| Core width Center (15) (mm) | 200 | 200 | 175 |
| Core Width Back (9) (mm) | 325 | 325 | 330 |
| Core Width Front (7) (mm) | 325 | 325 | 325 |
| Total Core Area (sqcm) | 1597 | 1597 | 1580 (±60) |
| Total Core Weight (g) | 103 | 103 | 110 (±5) |
| Front Half Section | | | |
| Airfelt/Fibrous Material | | | |
| Area (sqcm) | 764 | 764 | 754 (±50) |
| Weight (g) | 43.5 | 43.5 | 46 (±3) |
| Basis Weigh (g/sqcm) | 0.056 | 0.056 | 0.062 |
| Absorbent Gel Material | | | |
| Area (sqcm) | 495 | 495 | 754 |
| Weight (g) | 4.5 | 4.5 | 6 (±0.5) |
| Basis Weight (g/sqcm) | 0.0091 | 0.0091 | 0.008 |
| Test Results Front Half | | | |
| Average Basis Capacity (g/g) | 9.2 | 9.2 | 8.6 |
| Back Half Section | | | |
| Airfelt/Fibrous Material | | | |
| Area (sqcm) | 833 | 833 | 826 |
| Weight (g) | 47.5 | 47.5 | 51 (±3) |
| Basis Weigh (g/sqcm) | 0.056 | 0.056 | 0.062 |
| Absorbent Gel Material | | | |
| Area (sqcm) | 495 | 495 | 826 |
| Weight (g) | 7.5 | 7.5 | 6 (±0.5) |
| Basis Weight (g/sqcm) | 0.015 | 0.015 | 0.0073 |
| Test Results Back Half | | | |
| Average Basis Capacity (g/g) | 10.9 | 10.9 | 8.6 |
| Run-Off (g) | zero | 17.5 | 33.6 |

What is claimed is:

1. Absorbent article comprising a liquid permeable topsheet, a liquid impermeable backsheet and an absorbent core interposed between the topsheet and the backsheet, the backsheet comprising a perimeter having a front waist edge and a back waist edge, the core comprising a layer of absorbent material which layer comprises:

a perimeter having two longitudinal edges, a front transverse edge, and a back transverse edge, a transverse center line located midway between the front transverse edge and the back transverse edge, a front half section located between the transverse centerline (16) and the front transverse edge and a back half section located between the transverse centerline (16) and the back transverse edge, characterised in that the average basis capacity of the absorbent material located in the front half section of the layer of absorbent material is lower than the average back capacity of the absorbent material located in the back half section (19) of the layer, a liquid barrier means being located between the transverse centerline of the layer and the back waist edge of the backsheet to prevent liquids from leaking to the back waist edge of the backsheet.

2. Absorbent article according to claim 1, wherein the ratio of the average basis capacity of the back half section and the average basis capacity of the front half section is between 1.1 and 3.

3. Absorbent article according to claim 1, further comprising absorbent gelling material, wherein between 55% and 100% by weight of the absorbent gelling material is located in the back half section.

4. Absorbent article according to claim 3, wherein the ratio of the average basis weight of the absorbent gelling material in the back half section and in the front half section is between 1.1 and 3.

5. Absorbent article according to claim 1, further comprising fibrous or foamed absorbent material, the ratio of the average basis weight of the fibrous or foamed absorbent material in the back half section and the front half section being between 1.1 and 3.

6. Absorbent article according to claim 1, wherein the barrier means is located between the back transverse edge of the layer of absorbent material and the back waist edge of the backsheet to prevent leakage of liquids from the back transverse edge to the back waist edge.

7. Absorbent article according to claim 1, wherein the barrier means comprises a liquid impervious sealing area extending along at least a part of the length of the back transverse edge of the layer of absorbent material, the topsheet and the backsheet being joined at the sealing area.

8. Absorbent article according to claim 7, wherein the topsheet is heat-bonded to the backsheet.

9. Absorbent article according to claim 7, wherein the topsheet is adhesively connected to the backsheet in the sealing area.

10. Absorbent article according to claim 1, wherein the topsheet has a liquid impervious area extending beyond the back transverse edge of the layer of absorbent material.

11. Absorbent article according to claim 1, wherein the backsheet comprises a back waist section extending beyond the back transverse edge of the layer of absorbent material, wherein the back waist section comprises a z-like inward fold forming the liquid barrier means, the inward fold comprising an inward section and an outward section, the inward section and the outward section being mutually connected along a fold line located in proximity to the back transverse edge of the layer of absorbent material, and fixing means attaching the fold line to the topsheet and attaching the outward section to the inward section.

12. Absorbent article according to claim 1, wherein an elastic material is positioned in a sealing area located between the back traverse edge of the layer of absorbent material and the back waist edge of the backsheet.

13. Absorbent article according to claim 1, wherein the barrier means comprise a stand-up barrier cuff comprising a proximal edge which is connected to the absorbent article and a distal edge comprising elasticized means for spacing the distal edge away from the topsheet.

14. Absorbent article according to claim 13, wherein the proximal edge is located between the back transverse edge of the layer of absorbent material and the waist transverse edge of the backsheet.

15. Absorbent article according to claim 2 wherein the ratio of the average basis capacity of the back half section and the average basis capacity of the front half section is between 1.2 and 3.

16. Absorbent article according to claim 3 wherein between 60% and 90% by weight of the absorbent gelling material is located in the back half section.

17. Absorbent article according to claim 16 wherein between 65% and 80% by weight of the absorbent gelling material is located in the back half section.

18. Absorbent article according to claim 4 wherein the ratio of the average basis weight of the absorbent gelling material in the back half section and in the front half section is between 1.2 and 3.

19. Absorbent article according to claim 18 wherein the ratio of the average basis weight of the absorbent gelling material in the back half section and in the front half section is between 1.3 and 3.

20. Absorbent article according to claim 5, wherein the ratio of the average basis weight of the fibrous or foamed absorbent material in the back half section and the front half section being between 1.2 and 3.

21. Absorbent article according to claim 20, wherein the ratio of the average basis weight of the fibrous or foamed absorbent material in the back half section and the front half section being between 1.3 and 3.

* * * * *

UNITED STATES PATENT AND TRADEMARK OFFICE
CERTIFICATE OF CORRECTION

PATENT NO. : 6,103,952
DATED : August 15, 2000
INVENTOR(S) : Peter Coles et al.

It is certified that error appears in the above-identified patent and that said Letters Patent is hereby corrected as shown below:

Column 20, line 61, after "and the backsheet," please insert --and an absorbent core interposed between the topsheet and the backsheet,--.

Column 21, line 4, "centerline (16)" should read --centerline--.

Column 21, line 6, "centerline (16)" should read --centerline--.

Column 21, line 10, "back capacity" should read --basis capacity--.

Column 21, line 11, "half section (19)" should read --half section--.

Column 22, line 14, "traverse" should read --transverse--.

Signed and Sealed this

Twenty-fourth Day of April, 2001

Attest:

NICHOLAS P. GODICI

Attesting Officer

Acting Director of the United States Patent and Trademark Office